United States Patent
Kano et al.

(10) Patent No.: US 11,304,928 B2
(45) Date of Patent: Apr. 19, 2022

(54) TABLET COMPRISING 1-(3-(2-(1-BENZOTHIOPHEN-5-YL)ETHOXY)PROPYL)AZETIDIN-3-OL OR SALT THEREOF

(71) Applicant: FUJIFILM Toyama Chemical Co., Ltd., Chuo-ku (JP)

(72) Inventors: Atsushi Kano, Toyama (JP); Hiroyuki Inaba, Toyama (JP); Tai Oura, Toyama (JP)

(73) Assignee: FUJIFILM Toyama Chemical Co., Ltd., Chuo-ku (JP)

( * ) Notice: Subject to any disclaimer, the term of this patent is extended or adjusted under 35 U.S.C. 154(b) by 0 days.

(21) Appl. No.: 16/063,833

(22) PCT Filed: Dec. 22, 2016

(86) PCT No.: PCT/JP2016/088352
§ 371 (c)(1),
(2) Date: Jun. 19, 2018

(87) PCT Pub. No.: WO2017/111005
PCT Pub. Date: Jun. 29, 2017

(65) Prior Publication Data
US 2018/0369194 A1    Dec. 27, 2018

(30) Foreign Application Priority Data
Dec. 25, 2015    (JP) .............................. JP2015-253928

(51) Int. Cl.
| | |
|---|---|
| *A61K 31/397* | (2006.01) |
| *A61K 9/28* | (2006.01) |
| *A61K 9/20* | (2006.01) |
| *A61K 47/12* | (2006.01) |
| *A61K 47/26* | (2006.01) |
| *A61K 47/32* | (2006.01) |
| *A61K 47/38* | (2006.01) |
| *A61P 25/02* | (2006.01) |

(52) U.S. Cl.
CPC .......... *A61K 31/397* (2013.01); *A61K 9/2054* (2013.01); *A61K 9/28* (2013.01); *A61K 47/12* (2013.01); *A61K 47/26* (2013.01); *A61K 47/32* (2013.01); *A61K 47/38* (2013.01); *A61P 25/02* (2018.01)

(58) Field of Classification Search
USPC ..................................................... 514/210.19
See application file for complete search history.

(56) References Cited

U.S. PATENT DOCUMENTS

| | | | |
|---|---|---|---|
| 2005/0070521 A1 | 3/2005 | Saitoh et al. | |
| 2006/0205709 A1 | 9/2006 | Kimura et al. | |
| 2009/0093453 A1 | 4/2009 | Iwakami et al. | |
| 2009/0209512 A1* | 8/2009 | Iwakami | A61K 31/397 514/210.19 |
| 2011/0229570 A1 | 9/2011 | Sugimoto et al. | |
| 2015/0045345 A1 | 2/2015 | Inaba et al. | |
| 2017/0165227 A1 | 6/2017 | Takahashi et al. | |

FOREIGN PATENT DOCUMENTS

| | | |
|---|---|---|
| EP | 2 011 796 A1 | 1/2009 |
| EP | 2 048 145 A1 | 4/2009 |
| EP | 2048145 * | 4/2009 |
| EP | 3100725 * | 7/2016 |
| RU | 2340331 | 12/2008 |
| RU | 2472493 | 1/2013 |
| WO | WO 03/035647 A1 | 5/2003 |
| WO | WO 2004/091605 A1 | 10/2004 |
| WO | 2005/074895 | 8/2005 |
| WO | WO 2007/125913 A1 | 11/2007 |
| WO | 2008/140772 | 11/2008 |
| WO | WO 2010/061846 A1 | 6/2010 |
| WO | WO 2013/125617 A1 | 8/2013 |
| WO | WO 2015/115582 A1 | 8/2015 |

OTHER PUBLICATIONS

Chandran (Design and Evaluationof Ethyl Cellulose Based Matrix Tablets of Ibuprofen with pH Modulated Release Kinetics, Indian J Pharm Sci. Sep.-Oct. 2008; 70(5): 596-602).*
International Search Report dated Feb. 14, 2017 in PCT/JP2016/088352 filed Dec. 22, 2016.
European Search Report dated Jul. 19, 2019 issued in corresponding European patent application No. 16878892.5.
Russian Office Action and Search Report (with English Translations) dated May 12, 2020, in corresponding Russian Appln. No. 2018127136.

* cited by examiner

*Primary Examiner* — Kathrien A Cruz
(74) *Attorney, Agent, or Firm* — Oblon, McClelland, Maier & Neustadt, L.L.P.

(57) ABSTRACT

A tablet which comprises (1) 1-(3-(2-(1-benzothiophen-5-yl)ethoxy)propyl)azetidin-3-ol or a salt thereof and (2) ethyl cellulose, said tablet having excellent elution properties and good moldability, remaining stable during prolonged storage, and exhibiting high impact resistance.

7 Claims, No Drawings

TABLET COMPRISING 1-(3-(2-(1-BENZOTHIOPHEN-5-YL)ETHOXY) PROPYL)AZETIDIN-3-OL OR SALT THEREOF

TECHNICAL FIELD

The present invention relates to a tablet comprising 1-(3-(2-(1-benzothiophen-5-yl)ethoxy)propyl)azetidin-3-ol or a salt thereof.

BACKGROUND ART 1-(3-(2-(1-Benzothiophen-5-yl)ethoxy)propyl)azetidin-3-ol (hereinafter also referred to as "Compound A") or a salt thereof is a compound having neuroprotective, nerve regeneration-promoting and neurite outgrowth actions, and useful as a therapeutic agent for central and peripheral neurological diseases (Patent Document 1). Compound A or a salt thereof also exhibits a neurogenesis-inducing action, and is useful for treating diseases in which neurogenesis induction is effective for the therapy or prevention (Patent Document 2). This compound further exhibits an action of enhancing a functional impairment-ameliorating effect by post-nerve injury rehabilitation, and is therefore useful as a post-nerve injury rehabilitation effect-enhancing agent (Patent Document 3).

Compound A or a salt thereof is orally administered. Therefore, there is a need for a tablet comprising Compound A or a salt thereof. However, Compound A or a salt thereof has properties such as low compression moldability, proneness to a tableting trouble (sticking), and insufficient preservation stability at high humidity.

So far, some tablets comprising Compound A or a salt thereof, lactose, microcrystalline cellulose and an excipient have been known (Patent Document 4). Besides, some tablets comprising Compound A or a salt thereof, which are excellent in dissolvability and moldability, and further stable during long-term preservation, have been also known (Patent Document 5).

PRIOR ART DOCUMENTS

Patent Document

Patent Document 1: Pamphlet of International Publication No. WO 2003/035647
Patent Document 2: Pamphlet of International Publication No. WO 2007/125913
Patent Document 3: Pamphlet of International Publication No. WO 2015/115582
Patent Document 4: Pamphlet of International Publication No. WO 2004/091605
Patent Document 5: Pamphlet of International Publication No. WO 2013/125617

SUMMARY OF INVENTION

Technical Problem

In the production of tablets, it is necessary that mixture powders for tableting are compactable. It is also necessary that uncoated tablets obtained by tableting have a sufficient strength against impact generated during the production process and during transportation. When strength against impact, i.e., impact strength of the uncoated tablets is low, the impact may peel the tablet surface, leading to failure of the tablet. Tablets that do not have a sufficient impact strength and are easily peeled off lead to generation of poor tablets in a production process after tableting. As a result, the proportion of tablets removed in the inspection process increases, and the productivity decreases.

It is an object of the present invention to provide a tablet comprising Compound A or a salt thereof, which is excellent in dissolvability and moldability, and stable during long-term preservation, and further excellent in impact strength.

Solution to Problem

Under such circumstances, as a result of intensive studies, the present inventors have found that a tablet comprising Compound A or a salt thereof and ethyl cellulose is excellent in dissolvability and moldability, and stable during long-term preservation, and further excellent in impact strength, thereby accomplishing the present invention.

The present invention provides the following.

[1] A tablet comprising: (1) 1-(3-(2-(1-benzothiophen-5-yl)ethoxy)propyl)azetidin-3-ol or a salt thereof; and (2) ethyl cellulose.
[2] The tablet according to [1], wherein a content of ethyl cellulose is 1 to 30% based on the tablet mass.
[3] The tablet according to [1] or [2], further comprising microcrystalline cellulose.
[4] The tablet according to any one of [1] to [3], further comprising a sugar or a sugar alcohol.
[5] The tablet according to any one of [1[ to [3], further comprising one or more selected from lactose, sucrose, fructose, glucose, mannitol, sorbitol, isomalt, maltitol, trehalose and xylitol.
[6] The tablet according to any one of [1] to [3], further comprising one or more selected from mannitol, sorbitol, isomalt, maltitol, trehalose and xylitol.
[7] The tablet according to any one of [1] to [3], further comprising mannitol.
[8] The tablet according to any one of [1] to [7], further comprising one or two selected from croscarmellose sodium and crospovidone.
[9] The tablet according to any one of [1] to [8], further comprising magnesium stearate.
[10] The tablet according to any one of [1] to [9], wherein the tablet is a film coated tablet.
[11] The tablet according to any one of [1] to [10], for therapy of diseases of the central nerve or the peripheral nerve.
[12] The tablet according to any one of [1] to [10], for treating diseases in which neurogenesis induction is effective for therapy or prevention.
[13] The tablet according to any one of [1] to [10], for enhancing an effect of post-nerve injury rehabilitation.

Advantageous Effects of Invention

The tablet of the present invention is excellent in dissolvability and moldability, and stable during long-term preservation, and further excellent in impact strength.

The tablet of the present invention is useful as a tablet comprising Compound A or a salt thereof.

DESCRIPTION OF EMBODIMENTS

The present invention will be described below in detail.

As used herein, % means percentage by mass, unless otherwise noted.

<Tablet>

The tablet of the present invention comprises Compound A or a salt thereof and ethyl cellulose.

The tablet of the present invention means an uncoated tablet or a film-coated tablet (hereinafter also referred to as an FC tablet).

The FC tablet refers to a tablet provided by coating an uncoated tablet with a coating agent such as a polymer compound.

The tablet is preferably an FC tablet.

The size of the tablet of the present invention, for example, in the case of a round tablet having a content of Compound A of 160 mg, may be 7.5 to 9.5 mm in diameter and 4 to 6 mm in thickness, and is preferably 8.0 to 9.5 mm in diameter and 4.3 to 5.6 mm in thickness.

When administering the tablet of the present invention, the dose and frequency can be appropriately selected depending on the age, the body weight and the symptom of a patient, but its pharmaceutically effective amount may be usually administered in one to several divided doses per day. 80 to 2,000 mg per day of Compound A may be usually administered in one to several divided doses.

<Compound A or a Salt Thereof>

Compound A or a salt thereof used in the present invention can be produced, for example, by a method described in International Publication No. WO 2003/035647.

The content rate of Compound A or a salt thereof may be 10 to 93%, is preferably 10 to 90%, is more preferably 20 to 90%, and is still more preferably 45 to 90%, to the tablet mass.

Examples of the salt of Compound A include salts with an acid having a basic group conventionally known in the art such as an amino group.

Examples of the salt with an acid having a basic group include a salt with a mineral acid such as hydrochloric acid, hydrobromic acid, nitric acid and sulfuric acid; a salt with an organic carboxylic acid such as formic acid, acetic acid, citric acid, oxalic acid, fumaric acid, maleic acid, succinic acid, malic acid, tartaric acid, aspartic acid, trichloroacetic acid and trifluoroacetic acid; and a salt with a sulfonic acid such as methanesulfonic acid, benzenesulfonic acid, p-toluenesulfonic acid, mesitylenesulfonic acid and naphthalenesulfonic acid.

Among the above-mentioned salts, preferable salts include pharmacologically acceptable salts, and maleate is more preferable.

Compound A or a salt thereof of the present invention includes solvates, hydrates and crystals of various shapes thereof..

<Ethyl Cellulose>

The ethyl cellulose used in the present invention is not particularly limited, but includes Ethocel 100 FP Premium (The Dow Chemical Company).

A content of ethyl cellulose may be 1 to 60%, is preferably 1 to 30%, and is more preferably 1 to 20%, based on the tablet mass.

Ethyl cellulose is preferably added in an uncoated tablet.

By adding ethyl cellulose in an uncoated tablet, it is possible to provide the uncoated tablet having an excellent impact strength.

<Microcrystalline Cellulose>

The tablet of the present invention preferably further contains microcrystalline cellulose.

Examples of the microcrystalline cellulose include one or two selected from Ceolus KG-1000 (Asahi Kasei Chemicals Corporation) and PROSOLV SMCC 50 (JRS PHARMA).

A content of microcrystalline cellulose is not particularly limited, but is preferably 0.5 to 3.0%, and more preferably 1.0 to 3.0%, based on the tablet mass.

<Sugar or Sugar Alcohol>

The tablet of the present invention preferably further contains a sugar or a sugar alcohol.

Examples of the sugar used in the present invention include one or more selected from lactose, sucrose, maltose, fructose, galactose and glucose.

Examples of the sugar alcohol used in the present invention include one or more selected form mannitol, sorbitol, erythritol, maltitol, trehalose, xylitol, isomalt and lactitol.

The sugar or sugar alcohol is preferably one or more selected form the sugars or sugar alcohols, more preferably one or more selected from lactose, sucrose, fructose, glucose, mannitol, sorbitol, isomalt, maltitol, trehalose and xylitol, still more preferably one or more selected from mannitol, sorbitol, isomalt, maltitol, trehalose and xylitol, and particularly preferably mannitol.

A content of the sugar or sugar alcohol may be 1 to 70%, and is preferably 1 to 50%, based on the tablet mass.

<Disintegrant>

The tablet of the present invention preferably further contains a disintegrant.

Examples of the disintegrant used in the present invention include one or more selected from a cellulose derivatives such as carmellose, carmellose calcium, croscarmellose sodium and low-substituted hydroxypropylcellulose; a starch derivative such as carboxymethyl starch sodium and partially pregelatinized starch; and a polypyrrolidone derivative such as crospovidone.

The disintegrant is preferably one or more selected from the cellulose derivatives and polypyrrolidone derivatives, and more preferably one or two selected from croscarmellose sodium and crospovidone.

A content of the disintegrant may be 0.1 to 10%, is preferably 0.1 to 7%, and is more preferably 0.5 to 5%, based on the tablet mass.

<Lubricant>

The tablet of the present invention preferably further contains a lubricant.

Examples of the lubricant used in the present invention include one or more selected from sodium stearyl fumarate, stearic acid, magnesium stearate, calcium stearate, talc and sucrose fatty acid esters.

The lubricant is preferably one or two selected from sodium stearyl fumarate and magnesium stearate, and more preferably magnesium stearate.

A content of the lubricant may be 0.1 to 3%, and is preferably 0.5 to 2%, based on the tablet mass.

<Additive>

The tablet of the present invention can contain an additive conventionally used for medicines in the amount in a range that does not impair the effect of the present invention.

Examples of the additive include an excipient, a binder, a taste masking agent, a colorant, a flavoring agent, a surfactant, a fluidizing agent, a plasticizer, a glossing agent and a coating agent.

Example of the excipient include one or more selected from a cyclodextrin such as α-cyclodextrin, β-cyclodextrin, γ-cyclodextrin, hydroxypropyl-β-cyclodextrin and sulfobutyl ether-β-cyclodextrin sodium; a starch such as corn starch, potato starch and partially pregelatinized starch; a phosphate such as calcium hydrogen phosphate and anhydrous calcium hydrogen phosphate; and a carbonate such as precipitated calcium carbonate.

Examples of the binder include one or more selected from hydroxypropyl cellulose, carmellose sodium, polyvinylpyrrolidone, polyvinyl alcohol, hypromellose and methyl cellulose.

Examples of the taste masking agent include one or more selected from aspartame, saccharin, stevia, thaumatin and acesulfame potassium.

Examples of the colorant include one or more selected from titanium oxide, ferric oxide, yellow ferric oxide, black iron oxide, Food Red No. 102, Food Yellow No. 4 and Food Yellow No. 5.

Examples of the flavoring agent include one or more selected from an essential oil such as orange oil, lemon oil, peppermint oil and pine oil; an essence such as orange essence and peppermint essence; a flavor such as cherry flavor, vanilla flavor and fruit flavor; a powdered flavor such as apple micron, banana micron, peach micron, strawberry micron and orange micron; vanillin; and ethyl vanillin.

Examples of the surfactant include one or more selected from sodium lauryl sulfate, dioctyl sodium sulfosuccinate, a polysorbate, a sorbitan fatty acid ester and a polyoxyethylene-hardened castor oil.

Examples of the fluidizing agent include one or two selected from a silicon dioxide such as light anhydrous silicic acid and hydrous silicon dioxide.

Examples of the plasticizer include one or more selected from triethyl citrate, macrogol, triacetin and propylene glycol.

Examples of the glossing agent include one or more selected from carnauba wax, white beeswax and yellow beeswax.

Examples of the coating agent include one or more selected from a polymer compound, a plasticizer, a colorant, a lubricant and a glossing agent.

Examples of the polymer compound used for the coating agent include hypromellose, aminoalkyl methacrylate copolymer E, aminoalkyl methacrylate copolymer RS, ethyl cellulose, cellulose acetate phthalate, hypromellose phthalate, hypromellose acetate succinate, methacrylic acid copolymer L, methacrylic acid copolymer LD and methacrylic acid copolymer S.

Examples of the lubricant used for the coating agent include talc.

The used amount of the polymer compound, the plasticizer, the colorant, the lubricant and the glossing agent is not particularly limited, and the amount to be required according to the purpose may be appropriately added.

These additives may be used alone or in combination of two or more. The added amount of the additive is not particularly limited, and the additive may be appropriately added so that it exhibits a sufficient effect depending on the particular purpose.

<Use>

The tablet of the present invention can be used for therapy of diseases of the central nerve or the peripheral nerve; for treating diseases in which neurogenesis induction is effective for the therapy or prevention; or for enhancing an effect of post-nerve injury rehabilitation.

Examples of diseases of the central nerve or the peripheral nerve include Alzheimer's disease.

Examples of diseases in which neurogenesis induction is effective for the therapy or prevention include psychiatric disorder and spinal cord injury, and preferably psychiatric disorder.

Examples of the psychiatric disorder include schizophrenia and a disease related thereto such as schizophrenia, schizotypal disorder, schizoaffective disorder and other non-organic psychotic disorder; a mood disorder such as manic episode, bipolar affective disorder (manic-depressive psychosis), depression episode, recurrent depressive disorder and persistent mood disorder; and a neurotic disorder such as phobic anxiety disorder, obsessive-compulsive disorder and adjustment disorder, and preferably schizophrenia, bipolar affective disorder (manic-depressive psychosis), depression episode and recurrent depressive disorder.

Examples of the treatment include therapy and prevention.

The post-nerve injury rehabilitation refers to a training process that is aimed at shortening a hospitalization period after nerve injury, earlier autonomic self-care and improvement of quality of life (QOL), and is performed for earlier amelioration of functional impairment due to nerve injury and/or for alleviation of functional impairment (for example, to recover functions to levels close to the function levels before nerve injury).

The post-nerve injury rehabilitation is performed, for example, in acute stage, recovery stage and/or maintenance stage, depending on the timing after nerve injury and the condition of the patient. Examples of the post-nerve injury rehabilitation include a motor dysfunction-amelioration training such as muscle strengthening, motion range training of a joint such as a finger joint and a knee joint, and movement training such as walking; a language dysfunction-amelioration training; and/or a cognitive dysfunction-amelioration training, and preferably a motor dysfunction-amelioration training.

The rehabilitation effect refers to amelioration and/or alleviation of functional impairment by performing rehabilitation.

Examples of the functional impairment ameliorated and/or alleviated by rehabilitation include functional impairment caused by nerve injury, specifically motor dysfunction, sensation dysfunction and language dysfunction, and preferably motor dysfunction and language dysfunction, more preferably motor dysfunction, and still more preferably extremities-motor dysfunction. However, it does not include mental dysfunction such as depressive symptom and cognitive dysfunction such as dementia.

Rehabilitation effect-enhancement refers to recovery of functions and/or alleviation of functional impairment in a shorter period of time than in the case of rehabilitation alone.

Examples of the disease for which a post-nerve injury rehabilitation effect-enhancing agent is effective include stroke, brain injury, spinal cord injury, a neurodegenerative disease and a demyelinating disease, and preferably stroke, brain injury and spinal cord injury.

<Production Method>

Examples of the method for producing the tablet of the present invention include a method of tableting granules obtained by wet granulation or dry granulation, or a direct tableting method.

Examples of the wet granulation include fluidized-bed granulation, wet crushing granulation, extrusion granulation and agitation granulation.

Examples of the dry granulation include compacting method, slugging method and briquetting method.

Examples of the preferred production method include a direct tableting method and a tableting method using dry granulation.

Examples of the preferred dry granulation include compacting method and slugging method, and compacting method is more preferred. Examples of the compacting method include a method in which a compressed product is produced using a roller compactor and crushed to obtain granulated particles. The roller pressure of the roller compactor varies depending on the machine type used, but is preferably 3 to 9 MPa when using TF-LABO or TF-MINI (both manufactured by Freund Corporation).

The production method by dry granulation is preferably a method comprising (1) adding a portion of a lubricant to Compound A or a salt thereof and mixing them; (2) granulating by dry granulation; (3) passing the obtained granulated powder through a sieve; (4) adding a remaining portion of the lubricant, a disintegrant, an excipient and an additive thereto and mixing them; and (5) tableting the mixture powder.

An impact strength evaluation method includes a method for measuring a hardness conventionally used as an indicator of moldability. However, as shown in the below-described Test Examples, even if the tablet hardness is sufficient, falling impact strength may not be sufficient. It is difficult to measure, using a production machine, the impact received by tablets during the actual production process. Therefore, development of a method of measuring, by a convenient means, the impact similar to the impact caused by the production machine has been desired.

The present inventors have found that a method for conveniently measuring impact strength comprising allowing a tablet to freely fall from a certain height on a stainless steel sieve and determining the degree of failure (hereinafter also referred to as falling test) is suitable as a testing method.

Evaluation criteria for the falling test were set based on the results of tablets already commercially available. The most preferable level at which defective tablets are hardly observed in the falling test is +++, and the level at which defective tablets are observed is +, and the intermediate level between them is ++. At the level of + at which defective tablets are observed, failure occurs during the production process, so that the proportion of tablets removed during the inspection process increases, resulting in a decrease in productivity.

EXAMPLES

Next, the usefulness of the tablet of the present invention will be described with reference to Test Examples, Examples and Comparative Examples, but the present invention is not limited to them.

Each of the produced tablets is a round tablet of approximately 8.5 mm in diameter and approximately 4.3 to 5.6 mm in thickness.

The salt of Compound A used was Compound A maleate passed through a sieve of 500 μm in mesh size.

Unless otherwise specified, each of the component used was as follows:

Mannitol: Parteck M200 (Merck KGaA), passed through a sieve of 850 μm in mesh size;

Ethyl cellulose: Ethocel 100 FP Premium (The Dow Chemical Company), passed through a sieve of 850 μm in mesh size;

Sorbitol: D(-)-Sorbitol (Wako Pure Chemical Industries, Ltd.), passed through a sieve of 850 μm in mesh size;

Isomalt: galenIQ™ 801 (BENEO-Palatinit GmbH company), passed through a sieve of 850 μm in mesh size;

Maltitol: Amalty MR-50 (Mitsubishi Shoji Foodtech Co., Ltd.), passed through a sieve of 850 μm in mesh size;

Trehalose: Trehalose P (Asahi Kasei Chemicals Corporation), passed through a sieve of 850 μm in mesh size;

Xylitol: Xylitol (NACALAI TESQUE, INC.), passed through a sieve of 850 μm in mesh size;

Lactose: Pharmatose 200M (DFE pharma), passed through a sieve of 850 μm in mesh size;

Sucrose: Frost sugar (Nissin Sugar Co., Ltd.), passed through a sieve of 850 μm in mesh size;

Glucose: Glucose (Wako Pure Chemical Industries, Ltd.), passed through a sieve of 850 μm in mesh size;

Fructose: D (-)-fructose (Wako Pure Chemical Industries, Ltd.), passed through a sieve of 850 μm in mesh size;

Methyl cellulose: METOLOSE SM-4 (Shin-Etsu Chemical Co., Ltd.), passed through a sieve of 850 μm in mesh size;

Hydroxypropyl methylcellulose: TC-5 M (Shin-Etsu Chemical Co., Ltd.), passed through a sieve of 850 μm in mesh size;

Low-substituted hydroxypropylcellulose: L-HPC LH-22 (Shin-Etsu Chemical Co., Ltd.), passed through a sieve of 850 μm in mesh size;

Crospovidone: Kollidon CL-SF (BASF), passed through a sieve of 850 μm in mesh size;

Microcrystalline cellulose: CEOLUS KG-1000 (Asahi Kasei Chemicals Corporation), passed through a sieve of 850 μm in mesh size;

Croscarmellose Sodium: Primellose (DMV Japan), passed through a sieve of 850 μm in mesh size;

Magnesium stearate (Merck KGaA), passed through a sieve of 300 μm in mesh size;

Coating agent: Opadry 03F44057, 00F440000 (hypromellose 2910: 71.5%, Macrogol 6000: 14.166%, talc: 7.167%, titanium oxide: 7.067%, ferric oxide: 0.1%) (Colorcon Japan); and Carnauba wax: Polishing Wax-105 (Nippon Wax Co., Ltd., Freund Corporation).

Unless otherwise specified, each of the apparatuses used was as follows:

Dry granulator: TF-LABO (roll pressure: 3 MPa; Freund Corporation);

Tableting machine: HT-P18A (HATA TEKKOSHO CO., LTD.); and

Film coater: DRC-200 (Powrex Corporation).

Test Example 1

The uncoated tablets of Examples 1 to 4, Comparative Examples 1 and 2, and their FC tablets were used as samples.

The uncoated tablet of Comparative Example 1 was produced according to the method described in Example 15 of Patent Document 3.

The hardness of the uncoated tablets was measured by the below-mentioned method. The uncoated tablets were also subjected to a falling test to assess the impact strength of the uncoated tablets. In addition, the dissolution rate of the FC tablets was measured.

<Hardness>

A tablet hardness tester (Tablet hardness tester 8M, manufactured by Dr. Schleuniger Pharmatron AG) was used to measure the hardness of uncoated tablets. The measurement was made six times. The average value was calculated and used as the hardness.

<Falling Test>

The impact strength of uncoated tablets was evaluated by a falling test. The falling test was performed in the following procedure.

(1) Fifteen tablets were allowed to freely fall ten times from a height of 80 cm on a sieve No. 6.5 for the Japanese Pharmacopoeia (made of stainless; mesh size: 2.80 mm). Chipping generated on the surface of each of the tablets was visually observed and scored according to the following criteria. Another fifteen tablets were subjected to the above process, and the total value of the score for 30 tablets was calculated.

(2) The test of (1) was performed three times, and the average value of the total values was calculated and assessed according to the following criteria.

Scores
  2: A tablet having a peeled portion of 2 mm or more in longitudinal diameter (large chipping)
  1: A tablet having a peeled portion of 1 mm or more and less than 2 mm in longitudinal diameter (small chipping)
  0: A tablet having a peeled portion of less than 1 mm in longitudinal diameter or no chipping (slight or no chipping)

Assessment
  +++: Less than 5.0
  ++: 5.0 or more and less than 10.0
  +: 10.0 or more <Dissolution Test>

FC tablets were subjected the dissolution test according to the Japanese Pharmacopoeia dissolution test (paddle method). The rotation number of the paddle was 50 rpm. Each of samples was charged into 900 mL of USP dissolution test solution (pH 6.8), the sample solution was collected after 15 minutes, and the dissolution rate (%) of Compound A was determined by spectrophotometry. The pH 6.8 dissolution test solution was prepared by dissolving 272.2 g of potassium dihydrogen phosphate in water, adding 179.2 mL of a 5 mol/L aqueous sodium hydroxide solution thereto, then adding water thereto to 2000 mL, taking 300 mL of the solution, and mixing it with 5700 mL of water.

The results are shown in Table 1.

TABLE 1

| | | Example 1 | Example 2 | Example 3 | Example 4 | Comparative Example 1 | Comparative Example 2 |
|---|---|---|---|---|---|---|---|
| Maleate of Compound A | (%) | 71.0 | 71.0 | 71.0 | 71.0 | 89.5 | 71.0 |
| Mannitol | (%) | 20.0 | 15.0 | 10.0 | 5.0 | 6.0 | 25.0 |
| Ethyl Cellulose | (%) | 5.0 | 10.0 | 15.0 | 20.0 | — | — |
| Crospovidone | (%) | 2.5 | 2.5 | 2.5 | 2.5 | — | 2.5 |
| Croscarmellose Sodium | (%) | 0.5 | 0.5 | 0.5 | 0.5 | 3.0 | 0.5 |
| Magnesium Stearate | (%) | 1.0 | 1.0 | 1.0 | 1.0 | 1.5 | 1.0 |
| Total Amount | (%) | 100 | 100 | 100 | 100 | 100 | 100 |
| Mass of Uncoated Tablet | (mg) | 315 | 315 | 315 | 315 | 250 | 315 |
| Hardness of Uncoated Tablet | (N) | 131 | 124 | 133 | 116 | 70 | 133 |
| Falling Test | | ++ | +++ | +++ | +++ | + | + |
| Dissolution Rate of FC Tablet | (%) | 86.4 | 91.2 | 87.0 | 85.9 | 85.2 | 95.5 |

The formula used in Comparative Example 1 is the formula described in International Publication No. WO 2013/125617.

The formula used in Comparative Example 2 is the same formula as in Comparative Example 1 except that a disintegrant, croscarmellose sodium was partly replaced by crospovidone and mannitol was increased.

The tablets of Comparative Example 1 had a level of +.

The tablets of Comparative Example 2 had a tablet hardness enhanced, but no significant improvement was observed in the falling test.

On the other hand, the tablets of Example 1 containing ethyl cellulose had a tablet hardness enhanced as well as exhibited much more excellent properties in the falling test. The FC tablets of Example 1 exhibited excellent dissolution properties.

The tablets of Examples 2 to 4 having the content of ethyl cellulose increased exhibited excellent properties in the falling test and excellent dissolution properties.

Test Example 2

The uncoated tablets of Examples 5 to 9 and Comparative Example 3, and their FC tablets were used as samples.

The hardness of the uncoated tablets was measured by the same manner as in Example 1. The uncoated tablets were also subjected to a falling test to assess the impact strength of uncoated tablets. In addition, the dissolution rate of FC the tablets was measured.

The results are shown in Table 2.

TABLE 2

|  |  | Example 5 | Example 6 | Example 7 | Example 8 | Example 9 | Comparative Example 3 |
|---|---|---|---|---|---|---|---|
| Maleate of Compound A | (%) | 71.0 | 71.0 | 71.0 | 71.0 | 71.0 | 71.0 |
| Mannitol | (%) | 20.5 | 19.5 | 17.5 | 12.5 | 7.5 | 22.5 |
| Ethyl Cellulose | (%) | 2.0 | 3.0 | 5.0 | 10.0 | 15.0 | — |
| Microcrystalline Cellulose | (%) | 2.5 | 2.5 | 2.5 | 2.5 | 2.5 | 2.5 |
| Crospovidone | (%) | 2.5 | 2.5 | 2.5 | 2.5 | 2.5 | 2.5 |
| Croscarmellose Sodium | (%) | 0.5 | 0.5 | 0.5 | 0.5 | 0.5 | 0.5 |
| Magnesium Stearate | (%) | 1.0 | 1.0 | 1.0 | 1.0 | 1.0 | 1.0 |
| Total Amount | (%) | 100 | 100 | 100 | 100 | 100 | 100 |
| Mass of Uncoated Tablet | (mg) | 315 | 315 | 315 | 315 | 315 | 315 |
| Hardness | (N) | 125 | 132 | 127 | 130 | 133 | 142 |
| Falling Test |  | +++ | +++ | +++ | +++ | +++ | + |
| Dissolution Rate of FC Tablet | (%) | 93.8 | 90.9 | 94.1 | 88.1 | 88.1 | 89.6 |

The formula of Comparative Example 3 contains microcrystalline cellulose but not ethyl cellulose.

The tablets of Comparative Example 3 had a level of +.

On the other hand, the tablets of Examples 5 to 9 in which microcrystalline cellulose was added in addition to ethyl cellulose exhibited excellent properties in the falling test.

When using ethyl cellulose in combination with microcrystalline cellulose, the tablets of Example 5 and 6 having a lower content of ethyl cellulose also exhibited excellent properties in the falling test.

Test Example 3

The uncoated tablets of Examples 7 and 10 to 18, and their FC tablets were used as samples.

The hardness of the uncoated tablets was measured by the same manner as in Example 1. The uncoated tablets were also subjected to a falling test to assess the impact strength of the uncoated tablets. In addition, the dissolution rate of the FC tablets was measured.

The results are shown in Tables 3 and 4.

TABLE 3

|  |  | Example 7 | Example 10 | Example 11 | Example 12 | Example 13 | Example 14 |
|---|---|---|---|---|---|---|---|
| Maleate of Compound A | (%) | 71.0 | 71.0 | 71.0 | 71.0 | 71.0 | 71.0 |
| Mannitol | (%) | 17.5 |  |  |  |  |  |
| Sorbitol | (%) |  | 17.5 |  |  |  |  |
| Isomalt | (%) |  |  | 17.5 |  |  |  |
| Maltitol | (%) |  |  |  | 17.5 |  |  |
| Trehalose | (%) |  |  |  |  | 17.5 |  |
| Xylitol | (%) |  |  |  |  |  | 17.5 |
| Lactose | (%) |  |  |  |  |  |  |
| Sucrose | (%) |  |  |  |  |  |  |
| Glucose | (%) |  |  |  |  |  |  |
| Fructose | (%) |  |  |  |  |  |  |
| Ethyl Cellulose | (%) | 5.0 | 5.0 | 5.0 | 5.0 | 5.0 | 5.0 |
| Microcrystalline Cellulose | (%) | 2.5 | 2.5 | 2.5 | 2.5 | 2.5 | 2.5 |
| Crospovidone | (%) | 2.5 | 2.5 | 2.5 | 2.5 | 2.5 | 2.5 |
| Croscarmellose Sodium | (%) | 0.5 | 0.5 | 0.5 | 0.5 | 0.5 | 0.5 |
| Magnesium Stearate | (%) | 1.0 | 1.0 | 1.0 | 1.0 | 1.0 | 1.0 |
| Total Amount | (%) | 100 | 100 | 100 | 100 | 100 | 100 |
| Mass of Uncoated Tablet | (mg) | 315 | 315 | 315 | 315 | 315 | 315 |
| Hardness of Uncoated Tablet | (N) | 127 | 172 | 192 | 173 | 145 | 146 |
| Falling Test |  | +++ | +++ | +++ | +++ | +++ | +++ |
| Dissolution Rate of FC Tablet | (%) | 94.1 | 85.0 | 85.1 | 89.1 | 88.5 | 87.6 |

TABLE 4

|  |  | Example 15 | Example 16 | Example 17 | Example 18 |
|---|---|---|---|---|---|
| Maleate of Compound A | (%) | 71.0 | 71.0 | 71.0 | 71.0 |
| Mannitol | (%) |  |  |  |  |
| Sorbitol | (%) |  |  |  |  |
| Isomalt | (%) |  |  |  |  |
| Maltitol | (%) |  |  |  |  |
| Trehalose | (%) |  |  |  |  |
| Xylitol | (%) |  |  |  |  |
| Lactose | (%) | 17.5 |  |  |  |
| Sucrose | (%) |  | 17.5 |  |  |
| Glucose | (%) |  |  | 17.5 |  |
| Fructose | (%) |  |  |  | 17.5 |
| Ethyl Cellulose | (%) | 5.0 | 5.0 | 5.0 | 5.0 |
| Microcrystalline Cellulose | (%) | 2.5 | 2.5 | 2.5 | 2.5 |
| Crospovidone | (%) | 2.5 | 2.5 | 2.5 | 2.5 |
| Croscarmellose Sodium | (%) | 0.5 | 0.5 | 0.5 | 0.5 |
| Magnesium Stearate | (%) | 1.0 | 1.0 | 1.0 | 1.0 |
| Total Amount | (%) | 100 | 100 | 100 | 100 |
| Mass of Uncoated Tablet | (mg) | 315 | 315 | 315 | 315 |

TABLE 4-continued

|  |  | Example 15 | Example 16 | Example 17 | Example 18 |
|---|---|---|---|---|---|
| Hardness of Uncoated Tablet | (N) | 151 | 159 | 136 | 143 |
| Falling Test |  | +++ | +++ | +++ | +++ |
| Dissolution Rate of FC Tablet | (%) | 88.0 | 88.7 | 87.4 | 87.5 |

The formula of each of the tablets of Examples 10 to 18 is the same formula as Example 7 except that mannitol is replaced by sorbitol, isomalt, maltitol, trehalose, xylitol, lactose, sucrose, glucose or fructose, respectively.

The tablets of Examples 10 to 18 exhibited excellent properties in the falling test and excellent dissolution properties.

Test Example 4

The uncoated tablets of Example 2 and Comparative Examples 4 to 6, and their FC tablets were used as samples.

The uncoated tablets were also subjected to a falling test in the same method as in Test Example 1 to assess the impact strength of the uncoated tablets. In addition, the dissolution rate of the FC tablets was measured.

The results are shown in Table 5.

TABLE 5

|  |  | Example 2 | Comparative Example 4 | Comparative Example 5 | Comparative Example 6 |
|---|---|---|---|---|---|
| Maleate of Compound A | (%) | 71.0 | 71.0 | 71.0 | 71.0 |
| Mannitol | (%) | 15.0 | 15.0 | 15.0 | 15.0 |
| Ethyl Cellulose | (%) | 10.0 |  |  |  |
| Methyl Cellulose | (%) |  | 10.0 |  |  |
| Hydroxypropyl Methylcellulose | (%) |  |  | 10.0 |  |
| Low-Substituted Hydroxypropyl-cellulose | (%) |  |  |  | 10.0 |
| Crospovidone | (%) | 2.5 | 2.5 | 2.5 | 2.5 |
| Croscarmellose Sodium | (%) | 0.5 | 0.5 | 0.5 | 0.5 |
| Magnesium Stearate | (%) | 1.0 | 1.0 | 1.0 | 1.0 |
| Total Amount | (%) | 100 | 100 | 100 | 100 |
| Mass of Uncoated Tablet | (mg) | 315 | 315 | 315 | 315 |
| Falling Test |  | +++ | + | + | + |
| Dissolution Rate of FC Tablet | (%) | 91.2 | 87.4 | 96.1 | 90.8 |

The formula of each of the tablets of Examples 4 to 6 is the same formula as Example 2 except that ethyl cellulose is replaced by a different cellulosic material.

The tablets of Comparative Examples 4 to 6 exhibited excellent dissolution properties but did not exhibit any excellent properties in the falling test.

Example 1

To 895.06 g of the malate of Compound A, 5.00 g of magnesium stearate was added, and the resultant was mixed for 30 minutes. This mixture powder was compression-molded using a dry granulating machine, and the molded solid product was sized. To 107.09 g of the obtained sized powder, 29.95 g of mannitol, 7.53 g of ethyl cellulose, 3.75 g of crospovidone and 0.76 g of croscarmellose sodium were added, and the resultant was mixed for 30 minutes. To this mixture powder, 0.92 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 2

To 895.06 g of the malate of Compound A, 5.00 g of magnesium stearate was added, and the resultant was mixed for 30 minutes. This mixture powder was compression-molded using a dry granulating machine, and the molded solid product was sized. To 107.16 g of the obtained sized powder, 29.45 g of mannitol, 15.03 g of ethyl cellulose, 3.76 g of crospovidone and 0.75 g of croscarmellose sodium were added, and the resultant was mixed for 30 minutes.

To this mixture powder, 0.90 g of magnesium stearate was added, and the resultant was mixed for 5 minutes. This obtained mixture powder was subjected to tableting at a tableting pressure of approximately 9 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 3

To 895.06 g of the malate of Compound A, 5.00 g of magnesium stearate was added, and the resultant was mixed for 30 minutes. This mixture powder was compression-molded using a dry granulating machine, and the molded solid product was sized. To 107.16 g of the obtained sized powder, 14.94 g of mannitol, 22.49 g of ethyl cellulose, 3.75 g of crospovidone and 0.75 g of croscarmellose sodium were added, and the resultant was mixed for 30 minutes. To this mixture powder, 0.92 g of magnesium stearate was added, and the resultant was mixed for 5 minutes. This obtained mixture powder was subjected to tableting at a tableting pressure of approximately 9 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 4

To 895.06 g of the malate of Compound A, 5.00 g of magnesium stearate was added, and the resultant was mixed for 30 minutes. The mixture powder was compression-molded using a dry granulating machine, and the molded solid product was sized. To 107.15 g of the obtained sized powder, 7.46 g of mannitol, 30.00 g of ethyl cellulose, 3.75 g of crospovidone and 0.74 g of croscarmellose sodium were added, and the resultant was mixed for 30 minutes. To this mixture powder, 0.90 g of magnesium stearate was added, and the resultant was mixed for 5 minutes. This obtained mixture powder was subject to tableting at a tableting pressure of approximately 8 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 5

To 467.39 g of the malate of Compound A, 2.61 g of magnesium stearate was added, and the resultant was mixed for 30 minutes. This mixture powder was compression-molded using a dry granulating machine, and the molded solid product was sized. To 107.14 g of the obtained sized powder, 30.71 g of mannitol, 3.00 g of ethyl cellulose, 3.74 g of microcrystalline cellulose, 3.76 g of crospovidone and 0.76 g of croscarmellose sodium were added, and the resultant was mixed for 30 minutes. To this mixture powder, 0.90 g of magnesium stearate was added, and the resultant was mixed for 5 minutes. This obtained mixture powder was subjected to tableting at a tableting pressure of approximately 9 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 6

To 467.39 g of the malate of Compound A, 2.61 g of magnesium stearate was added, and the resultant was mixed for 30 minutes. This mixture powder was compression-molded using a dry granulating machine, and the molded solid product was sized. To 107.13 g of the obtained sized powder, 29.23 g of mannitol, 4.50 g of ethyl cellulose, 3.75 g of microcrystalline cellulose, 3.75 g of crospovidone and 0.77 g of croscarmellose sodium were added, and the resultant was mixed for 30 minutes. To this mixture powder, 0.91 g of magnesium stearate was added, and the resultant was mixed for 5 minutes. This obtained mixture powder was subjected to tableting at a tableting pressure of approximately 9 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 7

To 1988.89 g of the malate of Compound A, 11.11 g of magnesium stearate was added, and the resultant was mixed for 30 minutes. This mixture powder was compression-molded using a dry granulating machine, and the molded solid product was sized. To 107.13 g of the obtained sized powder, 26.21 g of mannitol, 7.50 g of ethyl cellulose, 3.75 g microcrystalline cellulose, 3.75 g of crospovidone and 0.75 g of croscarmellose sodium were added, and the resultant was mixed for 30 minutes. To this mixture powder, 0.90 g of magnesium stearate was added, and the resultant was mixed for 5 minutes. This obtained mixture powder was subjected to tableting at a tableting pressure of approximately 7 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 8

To 1988.89 g of the malate of Compound A, 11.11 g of magnesium stearate was added, and the resultant was mixed for 30 minutes. This mixture powder was compression-molded using a dry granulating machine, and the molded solid product was sized. To 107.13 g of the obtained sized powder, 18.71 g of mannitol, 15.00 g of ethyl cellulose, 3.75 g microcrystalline cellulose, 3.75 g of crospovidone and 0.75 g of croscarmellose sodium were added, and the resultant was mixed for 30 minutes. To this mixture powder, 0.90 g of magnesium stearate was added, and the resultant was mixed for 5 minutes. This obtained mixture powder was subjected to tableting at a tableting pressure of approximately 7 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 9

To 1988.89 g of the malate of Compound A, 11.11 g of magnesium stearate was added, and the resultant was mixed for 30 minutes. This mixture powder was compression-molded using a dry granulating machine, and the molded solid product was sized. To 107.13 g of the obtained sized powder, 11.21 g of mannitol, 22.50 g of ethyl cellulose, 3.75 g microcrystalline cellulose, 3.75 g of crospovidone and 0.76 g of croscarmellose sodium were added, and the resultant was mixed for 30 minutes. To this mixture powder, 0.90 g of magnesium stearate was added, and the resultant was mixed for 5 minutes. This obtained mixture powder was subjected to tableting at a tableting pressure of approximately 7 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 10

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.14 g of the obtained sized powder, 24.50 g of sorbitol, 7.03 g of ethyl cellulose, 3.50 g microcrystalline cellulose, 3.51 g of crospovidone and 0.71 g of croscarmellose sodium were added, and the resultant was mixed for 30 minutes. To this mixture powder, 0.84 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 11

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.03 g of the obtained sized powder, 24.53 g of isomalt, 7.00 g of ethyl cellulose, 3.50 g microcrystalline cellulose, 3.50 g of crospovidone and 0.70 g of croscarmellose sodium were added, and the resultant was mixed for 30 minutes. To this mixture powder, 0.84 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 12

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.47 g of the obtained sized powder, 24.52 g of maltitol, 7.02 g of ethyl cellulose, 3.50 g microcrystalline cellulose, 3.50 g of crospovidone and 0.70 g of croscarmellose sodium were added, and the resultant was mixed for 30 minutes. To this mixture powder, 0.84 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 13

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.98 g of the obtained sized powder, 24.57 g of trehalose, 7.01 g of ethyl cellulose, 3.53 g microcrystalline cellulose, 3.52 g of crospovidone and 0.70 g of croscarmellose sodium were added, and the resultant was mixed for 30 minutes. To this mixture powder, 0.85 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 14

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.40 g of the obtained sized powder, 24.52 g of xylitol, 7.03 g of ethyl cellulose, 3.50 g microcrystalline cellulose, 3.53 g of crospovidone and 0.70 g of croscarmellose sodium were added, and the resultant was mixed for 30 minutes. To this mixture powder, 0.84 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 15

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.03 g of the obtained sized powder, 24.51 g of lactose, 7.04 g of ethyl cellulose, 3.51 g microcrystalline cellulose, 3.50 g of crospovidone and 0.70 g of croscarmellose sodium were added, and the resultant was mixed for 30 minutes. To this mixture powder, 0.84 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 16

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.13 g of the obtained sized powder, 24.51 g of sucrose, 7.03 g of ethyl cellulose, 3.52 g microcrystalline cellulose, 3.50 g of crospovidone and 0.70 g of croscarmellose sodium were added, and the resultant was mixed for 30 minutes. To this mixture powder, 0.84 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 17

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.14 g of the obtained sized powder, 24.51 g of glucose, 7.03 g of ethyl cellulose, 3.50 g microcrystalline cellulose, 3.51 g of crospovidone and 0.70 g of croscarmellose sodium were added, and the resultant was mixed for 30 minutes. To this mixture powder, 0.84 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Example 18

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.01 g of the obtained sized powder, 24.51 g of fructose, 7.04 g of ethyl cellulose, 3.52 g microcrystalline cellulose, 3.52 g of crospovidone and 0.70 g of croscarmellose sodium were added, and the resultant was mixed for 30 minutes. To this mixture powder, 0.84 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Comparative Example 1

To 895.06 g of the malate of Compound A, 5.00 g of magnesium stearate was added, and the resultant was mixed for 30 minutes. This mixture powder was compression-molded using a dry granulating machine, and the molded solid product was sized. To 135.17 g of the obtained sized powder, 9.00 g of mannitol and 4.49 g of croscarmellose sodium were added, and the resultant was mixed for 30 minutes. To this mixture powder, 1.51 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain FC tablets.

Comparative Example 2

To 895.06 g of the malate of Compound A, 5.00 g of magnesium stearate was added, and the resultant was mixed for 30 minutes. This mixture powder was compression-molded using a dry granulating machine, and the molded solid product was sized. To 107.12 g of the obtained sized powder, 37.43 g of mannitol, 3.76 g of crospovidone and 0.75 g of croscarmellose sodium were added, and the resultant was mixed for 30 minutes. To this mixture powder, 0.90 g of magnesium stearate was added, and the resultant was mixed for 5 minutes. This obtained mixture powder was subjected to tableting at a tableting pressure of approximately 10 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Comparative Example 3

To 1988.89 g of the malate of Compound A, 11.11 g of magnesium stearate was added, and the resultant was mixed for 30 minutes. This mixture powder was compression-molded using a dry granulating machine, and the molded solid product was sized. To 107.13 g of the obtained sized powder, 33.71 g of mannitol, 3.75 g of microcrystalline cellulose, 3.75 g of crospovidone and 0.75 g of croscarmellose sodium were added, and the resultant was mixed for 30 minutes. To this mixture powder, 0.90 g of magnesium stearate was added, and the resultant was mixed for 5 minutes. This obtained mixture powder was subjected to tableting at a tableting pressure of approximately 8 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Comparative Example 4

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.27 g of the obtained sized powder, 21.08 g of mannitol, 14.03 g of methyl cellulose, 3.51 g of crospovidone and 0.70 g of croscarmellose sodium were added, and the resultant was mixed for 30 minutes. To this mixture powder, 0.84 g of magnesium stearate was added, and the resultant was mixed for 5 minutes. This obtained mixture powder was subjected to tableting at a tableting pressure of approximately 2 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Comparative Example 5

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.46 g of the obtained sized powder, 21.06 g of mannitol, 14.04 g of hydroxypropyl methylcellulose, 3.52 g of crospovidone and 0.70 g of croscarmellose sodium were added, and the resultant was mixed for 30 minutes. To this mixture powder, 0.84 g of magnesium stearate was added, and the resultant was mixed for 5 minutes. This obtained mixture powder was subjected to tableting at a tableting pressure of approximately 2 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

Comparative Example 6

To 1790.07 g of the malate of Compound A, 10.07 g of magnesium stearate was added, and the resultant was mixed for 30 minutes. This mixture powder was compression-molded using a dry granulating machine, and the molded solid product was sized. To 100.54 g of the obtained sized powder, 21.09 g of mannitol, 14.02 g of low-substituted hydroxypropylcellulose, 3.50 g of crospovidone and 0.71 g of croscarmellose sodium were added, and the resultant was mixed for 30 minutes. To this mixture powder, 0.84 g of magnesium stearate was added, and the resultant was mixed for 5 minutes. This obtained mixture powder was subjected to tableting at a tableting pressure of approximately 6 kN using a pestle having a double rounded surface with a tablet diameter of 8.5 mm to obtain round uncoated tablets of 315 mg per tablet. The uncoated tablets were coated with 9 mg of a coating agent per tablet, followed by adding a minute amount of carnauba wax thereto to obtain FC tablets.

INDUSTRIAL APPLICABILITY

The tablet of the present invention is useful as a tablet which is excellent in dissolvability and moldability, and stable during long-term preservation, and further excellent in impact strength.

The invention claimed is:

1. A tablet having improved impact strength comprising:
   (1) 1-(3-(2-(1-benzothiophen-5-yl)ethoxy)propyl)azetidin-3-ol or a salt thereof;
   (2) 2-5% based on the mass of the tablets ethyl cellulose
   (3) 0.5 to 3% based on the mass of the tablets of microcrystalline cellulose;
   (4) mannitol; and
   (5) from 0.1 to 10% based on the tablet mass of a disintegrant selected from the group consisting of croscarmellose sodium, crospovidone and mixtures thereof; and
   the tablet's impact strength is greater than that of a tablet of the same composition except not comprising ethyl cellulose when measured in the falling impact test.

2. The tablet according to claim 1, further comprising magnesium stearate.

3. The tablet according to claim 1, wherein the tablet is a film coated tablet.

4. A method for therapy of a disease of the central nerve or the peripheral nerve, comprising administering the tablet according to claim 1 to a subject in need thereof.

5. A method for treating a disease in which neurogenesis induction is effective for therapy, comprising administering the tablet according to claim 1 to a subject in need thereof.

6. A method for enhancing an effect of post-nerve injury rehabilitation, comprising administering the tablet according to claim 1 to a subject in need thereof.

7. The tablet according to claim 1, wherein the tablet is an uncoated tablet.

* * * * *